US012759956B2

(12) United States Patent
Bian

(10) Patent No.: US 12,759,956 B2
(45) **Date of Patent: *Oct. 13, 2026**

(54) METHOD FOR PREPARING GREEN METHANOL, GREEN ETHYLENE GLYCOL AND CARBON REDUCTION PET

(71) Applicant: JIANGSU ZHONGLU TECHNOLOGY DEVELOPMENT CORPORATION LIMITED, Suzhou (CN)

(72) Inventor: Shuchang Bian, Suzhou (CN)

(73) Assignee: JIANGSU ZHONGLU TECHNOLOGY DEVELOPMENT CORPORATION LIMITED, Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 19/233,715

(22) Filed: Jun. 10, 2025

(65) Prior Publication Data

US 2026/0070866 A1 Mar. 12, 2026

(30) Foreign Application Priority Data

Sep. 10, 2024 (CN) ......................... 202411263121.5

(51) Int. Cl.
*C07C 29/154* (2006.01)
*B01J 23/80* (2006.01)
(Continued)

(52) U.S. Cl.
CPC ............. *C07C 29/154* (2013.01); *B01J 23/80* (2013.01); *B01J 23/8472* (2013.01); *C07C 31/04* (2013.01)

(58) Field of Classification Search
CPC ..... C07C 29/154; C07C 31/04; C07C 29/152; C07C 1/20; C07C 29/106; B01J 23/80;
(Continued)

(56) References Cited

U.S. PATENT DOCUMENTS

2007/0040289 A1* 2/2007 Pilling ..................... B01D 3/22 261/114.5
2012/0323051 A1* 12/2012 Powell .................... C07C 29/00 568/913
(Continued)

FOREIGN PATENT DOCUMENTS

| | | | | | |
|---|---|---|---|---|---|
| CN | 101757943 | A | | 6/2010 | |
| CN | 114315514 | A | | 4/2022 | |
| CN | 114634400 | A | | 6/2022 | |
| CN | 115851696 | A | * | 3/2023 | ............... C25B 3/26 |
| JP | 10216522 | A | | 8/1998 | |

OTHER PUBLICATIONS

Eliasson et al., "Hydrogenation of Carbon Dioxide to Methanol with a Discharge-Activated Catalyst", Jul. 11, 1998, Industrial & Engineering Chemistry Research, vol. 37, pp. 3350-3357 (Year: 1998).*
(Continued)

*Primary Examiner* — Fereydoun G Sajjadi
*Assistant Examiner* — Y. Lynnette Kelly-O'Neill
(74) *Attorney, Agent, or Firm* — Dinsmore & Shohl LLP

(57) ABSTRACT

The present disclosure relates to a method for preparing green methanol, green ethylene glycol and carbon reduction PET. The method comprises the following steps: collecting and purifying a byproduct high-concentration carbon dioxide gas stream in a petroleum refining process into high-purity carbon dioxide, and then carrying out hydrogenation reaction in two-stage fixed bed reactors in sequence to prepare green methanol, the first-stage fixed bed reactor comprises at least two reaction towers arranged in parallel and filled with copper-zinc-calcium-magnesium-aluminum hydrogenation catalysts, and the second-stage fixed bed reactor comprises at least one reaction tower filled with copper-zirconium-titanium-vanadium deposition hydrogenation catalyst. The green methanol can be prepared into ethylene glycol through an MTO process, ethylene oxidation
(Continued)

and ethylene oxide hydrolysis. A carbon reduction PET can be prepared through esterification reaction and polymerization reaction. In the esterification and polymerization processes, specific esterification catalysts and composite stabilizers are added to improve the performance.

15 Claims, 1 Drawing Sheet

(51) Int. Cl.
*B01J 23/847* (2006.01)
*C07C 31/04* (2006.01)

(58) Field of Classification Search
CPC ...... B01J 23/8472; B01J 35/19; B01J 8/0242; B01J 35/40; B01J 35/55; B01J 35/56; B01J 35/613; B01J 35/615; B01J 37/03; B01J 37/035; B01J 37/08; B01J 37/10; Y02P 20/52; C08G 63/183; C07D 301/03; C07D 303/04
USPC ........................................................ 518/713
See application file for complete search history.

(56) References Cited

U.S. PATENT DOCUMENTS

| | | | | |
|---|---|---|---|---|
| 2014/0308597 | A1 | 10/2014 | Tsang | |
| 2015/0133699 | A1* | 5/2015 | Urakawa | B01J 23/72 568/840 |
| 2017/0267538 | A1* | 9/2017 | Novek | H02K 7/1823 |
| 2019/0076828 | A1 | 3/2019 | Almusaiteer et al. | |
| 2023/0391698 | A1 | 12/2023 | Grasso et al. | |
| 2024/0140891 | A1 | 5/2024 | Cassidy et al. | |

OTHER PUBLICATIONS

Mirvakili et al., "Modeling and assessment of novel configurations to enhance methanol production in industrial mega-methanol synthesis plant", Sep. 2019, Journal of the Taiwan Institute of Chemical Engineers, pp. 1-14 (Year: 2019).*

Atsbha et al., "Techno-Economic and Environmental Analysis for Direct Catalytic Conversion of CO2 to Methanol and Liquid/High-Calorie-SNG Fuels", May 29, 2021, Catalysts, vol. 11, No. 687, pp. 1-14 (Year: 2021).*

* cited by examiner

METHOD FOR PREPARING GREEN METHANOL, GREEN ETHYLENE GLYCOL AND CARBON REDUCTION PET

CROSS-REFERENCE TO RELATED APPLICATIONS

This application claims the benefit of priority to Chinese Patent Application No. 202411263121.5 filed on Sep. 10, 2024, and the entire disclosure is hereby incorporated by reference.

TECHNICAL FIELD

The present disclosure belongs to the field of petrochemical industry and polyester chemical technology, and particularly relates to a method for preparing green methanol, green ethylene glycol and carbon reduction PET.

BACKGROUND

Chemical fiber industry occupies a very important position in the national economy, polyethylene terephthalate fiber (PET, belongs to polyester fiber) accounts for more than 85% of the total chemical fiber, is the largest output, the most widely used chemical fiber varieties. Under the multiple challenges of increasingly severe climate change, environmental protection concept and resource shortage and the drive of the “double carbon” vision, circular economy and sustainable development model has gradually become an important direction of development. Ethylene glycol is one of the main raw materials for the production of polyester, at present, it is mainly produced by petroleum-based ethylene oxide hydration method and coal chemical method, and the development of high-purity green ethylene glycol industrial production technology is one of the technical problems to be solved in the process of green low-carbon transformation of polyester fiber industry.

In recent years, with the gradual depletion of fossil fuels such as oil, coal and natural gas, modern chemical industry based on the consumption of fossil raw materials will be greatly changed, with the increasing greenhouse gases being destroyed; a large number of carbon dioxide emissions is the biggest problem of modern life to the earth’s atmosphere pollution, is the direct cause of global warming and the extreme weather in recent years.

With the development of green sustainable, biodegradable, carbon reduction and environmental protection new technologies, including solar energy utilization driven by photovoltaic industry, wind power generation technology driven by light weight and high strength materials such as carbon fiber, large capacity hydropower and the developing tidal power generation technology and a series of new energy technologies, a new energy field is provided, the consumption of fossil energy is greatly reduced, the proportion of these green energy is further improved.

The development of industrial carbon capture technology can reduce the emission of carbon dioxide greenhouse gas by means of sequestration and chemical conversion, but the method of carbon dioxide sequestration can only control the emission of greenhouse gas for a short time, and cannot fundamentally solve the problem of carbon dioxide emission. The development of large capacity carbon dioxide capture and purification PSA device technology can simply improve the content of carbon dioxide and purify the quality of carbon dioxide, while the research on the chemical conversion technology of carbon dioxide supported by green energy has been rapidly developed from laboratory research and development to pilot scale-up and industrialization technology stage. Using carbon dioxide as raw material and reacting with hydrogen to synthesize methanol, on the one hand, $CO_2$ in industrial waste gas can be captured, and large-scale thermal power, refining tail gas and other carbon dioxide gas streams with high concentration can be improved to high purity level by simple purification technology to meet the quality requirements of carbon dioxide hydrogenation to prepare methanol. On the other hand, various green energy can be used to electrolyze hydrogen to provide completely green hydrogen resources. Carbon dioxide hydrogenation to methanol technology can provide a new and convenient idea for methanol production and energy storage.

The core of the technology for preparing methanol from carbon dioxide and hydrogen is the selection and synthesis of a hydrogenation catalyst, which is a carbonyl catalyst. Mainstream types include copper-zinc-aluminum oxide, copper-zinc carbonate compounds, and novel catalysts composed of multiple metal elements. In actual operation, although the catalysts have good catalytic efficiency and selectivity, they all have the defect of poor hydrolysis resistance. The main reason is that zinc oxide and aluminum oxide, etc. can combine with water to form hydroxides under the condition of high temperature and the presence of moisture (a small amount of water generated in the reaction process), resulting in the loss of effective components of the catalyst which is the corresponding oxides.

SUMMARY

The present disclosure provides a method for preparing green methanol, which is green and environment-friendly, and can significantly improve the conversion rate and reaction selectivity of carbon dioxide.

The present disclosure also provides a method for preparing ethylene glycol. The method is environmentally friendly and can achieve low-carbon production.

The present disclosure also provides a method for preparing carbon reduction PET. The method uses ethylene glycol prepared based on carbon dioxide capture as one of the polymerization monomers and can achieve environmentally friendly production of polyester and ensure that the performance of polyester can basically reach the performance level of polyester prepared by the petrochemical method with ethylene glycol.

To achieve the above object, the present disclosure adopts the following technical scheme:

A method for preparing methanol, the method using carbon dioxide and hydrogen as raw materials to prepare the methanol by hydrogenation reaction, wherein, the hydrogenation reaction is carried out in two-stage fixed bed reactors in sequence, the first-stage fixed bed reactor comprises at least two reaction towers arranged in parallel, and the second-stage fixed bed reactor comprises at least one reaction tower, each reaction tower of the first-stage fixed bed reactor is filled with a copper-zinc-calcium-magnesium-aluminum hydrogenation catalyst, and each reaction tower of the second-stage fixed bed reactor is filled with a copper-zirconium-titanium-vanadium deposition hydrogenation catalyst;

the copper-zinc-calcium-magnesium-aluminum hydrogenation catalyst being columnar and having a porous structure, comprising a supporting carrier and an active component, the active component comprising copper oxide, zinc oxide, calcium oxide, magnesium oxide and aluminum oxide, the copper-zirconium-titanium-vanadium deposition hydrogenation catalyst being columnar and having a porous structure, comprising a supporting carrier, a nano silicon dioxide carrier, and a porous deposition catalyst layer on the surface of the nano silicon dioxide carrier, the porous deposition catalyst layer comprising copper oxide, zirconium oxide, titanium oxide and vanadium oxide, and the supporting carrier comprising graphite, activated carbon and a binder.

In the present disclosure, the parallelly arranged reaction towers refer to that materials are parallelly fed into each reaction tower to react, each parallelly arranged reaction tower simultaneously processes materials, different materials simultaneously react in different reaction towers, and the total amount of the reaction materials is the sum of the material amounts of each reaction tower, instead of that the materials sequentially react in each reaction tower.

The present disclosure uses a novel catalyst which is columnar and has a porous structure, and simultaneously, a parallel multi-tower design is adopted for the first-stage methanol reactor and a single or double tower design is adopted for the second-stage methanol reactor, and the conversion rate and selectivity of carbon dioxide when synthesizing methanol from carbon dioxide are improved. The segmented reaction effectively prolongs the residence time of the mixed gas flow in the main reaction zone, and effectively improves the conversion rate of a single cycle reaction. The copper-zirconium-titanium-vanadium deposition hydrogenation catalyst has a good catalytic effect and a hydrolysis inactivation resistance, is not affected by water in reaction byproducts, and has stable oxide deposits as the active components in the porous deposition catalyst layer.

In some embodiments, the first-stage fixed bed reactor comprises 2-6 reaction towers arranged in parallel.

In some embodiments, the first-stage fixed bed reactor comprises 3-5 reaction towers arranged in parallel.

In some embodiments, the second-stage fixed bed reactor comprises 1-2 reaction towers.

In some embodiments, the second-stage fixed bed reactor comprises 2 reaction towers arranged in parallel.

In some embodiments, each reaction tower arranged in parallel in the first-stage fixed bed reactor and the second-stage fixed bed reactor is provided with a nitrogen inlet and a nitrogen outlet.

In some embodiments, the method controls one reaction tower in the first-stage fixed bed reactor to not perform the hydrogenation reaction as a standby tower, and also controls one reaction tower in the second-stage fixed bed reactor to not perform the hydrogenation reaction as a standby tower; when the catalyst in the reaction tower performing the hydrogenation reaction in the first-stage fixed bed reactor or the second-stage fixed bed reactor reaches its service cycle, the reaction tower is switched to the standby tower; and the reaction tower is subjected to nitrogen purging to regenerate the catalyst, and the temperature of the nitrogen is 300-400° C.

In some embodiments, in the copper-zinc-calcium-magnesium-aluminum hydrogenation catalyst, the supporting carrier accounts for 40%-50% by weight, and the active component accounts for 50%-60% by weight.

In some embodiments, in the copper-zinc-calcium-magnesium-aluminum hydrogenation catalyst, the copper oxide accounts for 30%-40% of the active component by weight, the zinc oxide accounts for 23%-30% of the active component by weight, the calcium oxide accounts for 4%-6% of the active component by weight, the magnesium oxide accounts for 14%-18% of the active component by weight, and the aluminum oxide accounts for 15%-20% of the active component by weight.

In some embodiments, the copper oxide accounts for 32%-38% of the active component by weight, the zinc oxide accounts for 24%-28% of the active component by weight, the calcium oxide accounts for 4.2%-5.8% of the active component by weight, the magnesium oxide accounts for 15%-17% of the active component by weight, and the aluminum oxide accounts for 16.0%-19.0% of the active component by weight.

In some embodiments, the copper oxide accounts for 34%-36% of the active component by weight, the zinc oxide accounts for 25%-27% of the active component by weight, the calcium oxide accounts for 4.5%-5.5% of the active component by weight, the magnesium oxide accounts for 15.5%-16.5% of the active component by weight, and the aluminum oxide accounts for 17.0%-18.0% of the active component by weight.

In some embodiments, in the copper-zirconium-titanium-vanadium deposition hydrogenation catalyst, the supporting carrier accounts for 40%-50%, the nano silicon dioxide carrier accounts for 20%-25%, and the porous deposition catalyst layer accounts for 25%-40% by weight.

In some embodiments, in the copper-zirconium-titanium-vanadium deposition hydrogenation catalyst, the copper oxide accounts for 40%-50%, the zirconium oxide accounts for 25%-35%, the titanium oxide accounts for 10%-15%, and the vanadium oxide accounts for 10%-15% of the porous deposition catalyst layer by weight.

In some embodiments, the copper oxide accounts for 42%-48%, the zirconium oxide accounts for 26%-34%, the titanium oxide accounts for 10.8%-14.2%, and the vanadium oxide accounts for 11.5%-13.5% of the porous deposition catalyst layer by weight.

In some embodiments, the copper oxide accounts for 43.5%-46.5%, the zirconium oxide accounts for 28%-32%, the titanium oxide accounts for 11.5%-13.5%, and the vanadium oxide accounts for 12%-13% of the porous deposition catalyst layer by weight.

In some embodiments, the specific surface area of the copper-zinc-calcium-magnesium-aluminum hydrogenation catalyst is 125-150 $m^2/g$.

In some embodiments, the length of the copper-zinc-calcium-magnesium-aluminum hydrogenation catalyst is 4-8 mm.

In some embodiments, the specific surface area of the copper-zirconium-titanium-vanadium deposition hydrogenation catalyst is 80-100 $m^2/g$.

In some embodiments, the length of the copper-zirconium-titanium-vanadium deposition hydrogenation catalyst is 4-8 mm.

In some embodiments, in the supporting carrier, the graphite accounts for 30%-35%, the activated carbon accounts for 45%-55%, and the binder accounts for 15%-20% by weight.

In some embodiments, the particle size of the graphite is 0.2-0.3 μm.

In some embodiments, the activated carbon is coconut shell carbon micro powder.

In some embodiments, the copper-zinc-calcium-magnesium-aluminum hydrogenation catalyst is prepared by a preparation method comprising the following steps: 1) mixing a water-soluble zinc salt solution, a water-soluble magnesium salt solution and a water-soluble aluminum salt solution to obtain a mixed solution; and adding an aqueous sodium hydroxide solution dropwise into the mixed solution to obtain a co-precipitation deposition suspension; 2) simultaneously adding an aqueous solution of water-soluble copper salt, an aqueous solution of water-soluble calcium salt and an aqueous sodium hydroxide solution dropwise into the co-precipitation deposition suspension; 3) adding an aqueous sodium bicarbonate solution to adjust the pH value of a reaction system; and aging by heating; 4) placing the reaction system in a high-pressure reaction kettle, and performing high-pressure blasting, dehydration treatment and re-dispersion of the reaction system into a suspension in water under the conditions of heating and stirring; 5) adding tetrabutyl silicate dropwise into the suspension; 6) filtering to form a filter cake, and adding graphite, activated carbon and a binder into the filter cake, and heating and shaping to obtain the copper-zinc-calcium-magnesium-aluminum hydrogenation catalyst.

The copper-zinc-calcium-magnesium-aluminum hydrogenation catalyst of the present application is a co-deposition porous nano multi-metal catalyst, and has excellent carbonyl hydrogenation catalytic activity and high selectivity. In high-pressure blasting, a high-pressure circulating pump is started, the high-temperature and high-pressure suspension is transported to a specially designed high-pressure blasting nozzle, the catalyst powder suspension after the dehydration reaction is suddenly blasted from the high-pressure and overheated water to the normal pressure condition, the submicron powder is blasted to the nano powder, and the porous area rate of the powder is greatly increased.

In some embodiments, the water-soluble zinc salt, the water-soluble magnesium salt, the water-soluble aluminum salt, the water-soluble copper salt and the water-soluble calcium salt are respectively selected from the sulfate, the acetate or the chloride of the corresponding metal element.

In some embodiments, the molar concentration of the water-soluble zinc salt in the mixed solution is 1.0-3.0 mol/L, preferably 2.0 mol/L.

In some embodiments, the molar concentration of the water-soluble magnesium salt in the mixed solution is 1.0-3.0 mol/L, preferably 2.0 mol/L.

In some embodiments, the molar concentration of the water-soluble aluminum salt in the mixed solution is 1.0-3.0 mol/L, preferably 2.5 mol/L.

In some embodiments, the molar concentration of the aqueous sodium hydroxide solution is 1.0-3.0 mol/L, preferably 2.5 mol/L.

In some embodiments, the molar concentration of the aqueous solution of the water-soluble copper salt is 1.0-3.0 mol/L, preferably 3.0 mol/L.

In some embodiments, the molar concentration of the aqueous solution of the water-soluble calcium salt is 1.0-3.0 mol/L, preferably 0.5 mol/L.

In some embodiments, the molar concentration of the aqueous sodium bicarbonate solution is 1.0-3.0 mol/L, preferably 2.0 mol/L.

In some embodiments, the dropwise adding in steps 1) and 2) is performed at 70-80° C.

In some embodiments, the dropwise adding in steps 1) and 2) is performed at a pH of 9.5-10.5.

In some embodiments, in step 3), the pH of the adjusted system is 9.5-10.5, preferably 10.0.

In some embodiments, the high-pressure blasting in step 4) is performed by a high-pressure blasting nozzle.

In some embodiments, in step 5), the dropwise adding of the tetrabutyl silicate is performed at 70-80° C. for 6-8 hours.

In some embodiments, the tetrabutyl silicate accounts for 100-150 ppm of the mass of the copper-zinc-calcium-magnesium-aluminum hydrogenation catalyst.

In some embodiments, in step 6), the temperature of the heating and shaping is 320-350° C.

In some embodiments, the copper-zirconium-titanium-vanadium deposition hydrogenation catalyst is prepared by a preparation method comprising the following steps: 1) simultaneously adding an aqueous solution of a water-soluble copper salt, a tetraalkyl zirconium, a tetraalkyl titanate, an aqueous sodium metavanadate solution, an aqueous sodium hydroxide solution, and an aqueous sodium carbonate solution dropwise on the nano silicon dioxide carrier, so that the porous deposition catalyst layer is formed on the nano silicon dioxide carrier after reaction; the alkyl group is a C1-6 alkyl group; and 2) filtering, adding graphite, activated carbon, and a binder into a filter cake, and performing heat treatment to obtain the copper-zirconium-titanium-vanadium deposition hydrogenation catalyst.

In some embodiments, the water-soluble copper salt is selected from one or both of copper sulfate and copper chloride.

In some embodiments, the tetraalkyl zirconium is tetraethyl zirconium.

In some embodiments, the tetraalkyl titanate is tetraisopropyl titanate.

In some embodiments, the molar concentration of the aqueous solution of the water-soluble copper salt is 1.0-3.0 mol/L, preferably 3.0 mol/L.

In some embodiments, the molar concentration of the aqueous sodium metavanadate solution is 1.0-3.0 mol/L, preferably 2.0 mol/L.

In some embodiments, the molar concentration of the aqueous sodium hydroxide solution is 1.0-3.0 mol/L, preferably 2.5 mol/L.

In some embodiments, the molar concentration of the aqueous sodium carbonate solution is 1.0-3.0 mol/L, preferably 2.0 mol/L.

In some embodiments, in step 1), the adding dropwise is performed at a pH of 9-11.

In some embodiments, in step 2), the temperature of the heat treatment is 50-600° C., and the time is 16-24 h.

In some embodiments, the first fixed bed reactor comprises an inner chamber and an outer chamber, the inner chamber comprises a plurality of horizontal arranged trays, and two adjacent trays are staggered, the outer chamber is designed as a tower, and the top, middle and bottom of the outer chamber are all designed with a plurality of groups of homogenizing trays, the copper-zinc-calcium-magnesium-aluminum hydrogenation catalyst is filled between the inner chamber and the homogenizing trays of the outer chamber, and a filter screen is arranged at the bottom of the outer chamber.

In present disclosure, the staggered design of the two adjacent trays means that the projections of the two trays on the horizontal plane are partially overlapped, for example, an upper tray is fixed on one side of the inner chamber, and the horizontal length of the upper tray is less than the diameter of the inner chamber, and an adjacent lower tray is fixed on the other side of the inner chamber, and the horizontal length of the lower tray is also less than the diameter of the inner chamber, and the projections of the two trays on the horizontal plane are partially overlapped, so that the gas flow can flow between the two adjacent trays, and the residence time of the gas flow is prolonged.

In some embodiments, the effective volumes of the inner chamber and the outer chamber are the same.

In some embodiments, the residence time of the reaction gas in the inner chamber and the outer chamber is the same. Thus, the stability of the entire reaction in the first-stage fixed bed reactor can be ensured.

In some embodiments, the residence time of the raw gas in the first-stage fixed bed reactor is 275-350 s, preferably, the residence time is 290-340 s, and more preferably, the residence time is 300-330 s.

In some embodiments, after the hydrogenation reaction of the first-stage fixed bed reactor is completed, the conversion rate of carbon dioxide is 64.0%-75.8%; preferably, the conversion rate is 66.5%-75.8%, and more preferably, the conversion rate is 70.5%-75.8%.

In some embodiments, the volume of the first-stage fixed bed reactor is 135-150 $m^3$, and the volume of the filled copper-zinc-calcium-magnesium-aluminum hydrogenation catalyst is 75-90 $m^3$.

In some embodiments, the volume of the second-stage fixed bed reactor is 135-150 $m^3$, and the volume of the filled copper-zirconium-titanium-vanadium deposition hydrogenation catalyst is 75-90 $m^3$.

In some embodiments, the residence time of the reaction system in the second-stage fixed bed reactor is 75-100 s.

In some embodiments, in the second-stage fixed bed reactor, the effective self-circulation ratio of the reaction system is 3.5-6.0.

The effective self-circulation ratio refers to the ratio of the total amount of the circulating materials to the total amount of the introduced materials re-supplied from outside.

In some embodiments, after the hydrogenation reaction of the second-stage fixed bed reactor is completed, the cumulative conversion rate of carbon dioxide is 92.4%-95.5%.

In some embodiments, the temperature of the first-stage fixed bed reactor is 150-350° C., and the pressure is 5.0-20.0 MPa.

In some embodiments, the temperature of the first-stage fixed bed reactor is 180-300° C., and the pressure is 7.5-15 MPa.

In some embodiments, the temperature of the first-stage fixed bed reactor is 260-280° C., and the pressure is 8.0-10 MPa.

In some embodiments, the temperature of the second-stage fixed bed reactor is 120-240° C., and the pressure is 10.0-20.0 MPa.

In some embodiments, the temperature of the second-stage fixed bed reactor is 150-200° C., and the pressure is 12.5-17.5 MPa.

In some embodiments, the temperature of the second-stage fixed bed reactor is 160-180° C., and the pressure is 14.0-15.0 MPa.

In some embodiments, the temperature of the third stage fixed bed reactor is 150-350° C., and the pressure is 5.0-20.0 MPa.

In some embodiments, the carbon dioxide is derived from by-products of a petroleum refining process.

In some embodiments, the by-products of the petroleum refining process contain 80%-90% carbon dioxide by volume. The carbon dioxide also contains a certain amount of low molecular weight alkanes, low molecular weight alkenes, water, and impurities such as organic low molecular weight gases containing sulfur, nitrogen, and phosphorus.

In some embodiments, the method further comprises the steps of filtering, water washing, ammonia water washing, removing solid suspensions, and pressure swing adsorption (PSA) treatment of the byproduct of the petroleum refining process, and after the step, the volume content of the carbon dioxide is 98.0%-99.5%.

In some embodiments, the carbon dioxide and hydrogen are mixed and pressurized, and then enter the first-stage fixed bed reactor from the bottom to perform a hydrogenation reaction, the gas stream after the reaction flows out from the bottom of the first-stage fixed bed reactor, enters a condenser to be condensed, and after depressurization, enters a methanol phase separation device to perform phase separation.

In some embodiments, the molar ratio of the carbon dioxide and hydrogen is 1:3-4.5.

In some embodiments, the gas stream (mainly unreacted carbon dioxide, hydrogen, methane, carbon monoxide, moisture, and the like) at the top of the methanol phase separation device and additional hydrogen are mixed and pressurized, and then enter a middle and lower part of the second-stage fixed bed reactor, the mixed gas stream performs a hydrogenation reaction in the second-stage fixed bed reactor, the liquid components (methanol obtained by the reaction and components with relatively heavy molecular weight) after the reaction flow out from the bottom of the second-stage fixed bed reactor, and enter the methanol phase separation device to perform phase separation.

In some embodiments, the volume of the additional hydrogen accounts for 4%-8% of the volume of the hydrogen fed into the first fixed bed reactor.

In some embodiments, the tail gas at the top of the second-stage fixed bed reactor is introduced into a pressure swing adsorption (PSA) hydrogen recovery device after depressurization treatment, and hydrogen is adsorbed, and then desorbed to obtain recovered hydrogen.

In some embodiments, the recovered hydrogen is used as the additional hydrogen entering the second-stage fixed bed reactor. The incompletely reacted mixed gas at the top of the methanol phase separation device shared by the first-stage and second-stage methanol reactors is pressurized by a compressor and introduced into the second-stage methanol reactor, and a large-scale circulation reaction mode is adopted.

In some embodiments, the tail gas after adsorbing hydrogen contains a small amount of carbon dioxide, methane, ethane, formaldehyde, acetaldehyde, trace hydrogen, and the like, and is sent to a tail gas incineration device for venting.

In some embodiments, the liquid crude methanol obtained from the methanol phase separation devices can be subjected to two-stage distillation separation, and the pressure of the second-stage distillation is higher than that of the first-stage distillation.

For the two-stage distillation separation system, the first-stage rectification adopts low-pressure rectification, the crude methanol is transported to the bottom of the first-stage distillation tower, the methanol is taken out from the top of the distillation tower and transported to a refined methanol product tank through cooling reflux, the heavy components at the bottom of the low-pressure distillation tower mainly contain 50%-60% methanol and other high-boiling by-products, and are transported to the middle of the second-stage methanol distillation tower through a circulating pump, high-quality methanol is further taken out from the top of the tower through distillation and transported to the refined methanol product tank after cooling, and the high-boiling components taken out from the bottom are transported to a fusel oil storage tank as fusel oil for further treatment.

The present disclosure also provides a method for preparing ethylene glycol, comprising the steps of preparing ethylene from methanol by MTO technology, preparing ethylene oxide by oxidizing the ethylene, and preparing ethylene glycol by hydrolyzing the ethylene oxide, the method further comprising the step of preparing methanol mentioned above in the present disclosure.

The ethylene glycol prepared by the method has good quality, can meet the requirements of conventional polyester esterification and polymerization reaction, and can obtain the green carbon reduction polyester meeting the requirements of fiber spinning.

The present disclosure also provides a method for preparing polyethylene terephthalate, comprising the steps of sequentially performing first esterification, second esterification, first prepolymerization, second prepolymerization, and final polymerization on terephthalic acid and ethylene glycol; the method further comprising the steps of preparing the ethylene glycol mentioned above, and adding an esterification catalyst and a composite stabilizer to the terephthalic acid and the ethylene glycol before performing the first esterification step; the esterification catalyst being selected from the group consisting of zinc acetate, manganese acetate, potassium acetate, sodium acetate, cobalt acetate, calcium acetate, and lithium acetate, or combinations thereof; the composite stabilizer comprising an amine stabilizer, sodium bisulfite, and a phosphorus stabilizer.

By using the PTA and the ethylene glycol prepared from the industrial by-product $CO_2$ gas stream as raw materials, slurry is prepared, esterification and polymerization are carried out, and the environment-friendly carbon reduction polyester can be prepared. In the esterification and polymerization process, the present disclosure uses the esterification catalyst and the composite stabilizer to prepare the environment-friendly carbon-reducing polyester, and the performance of the environment-friendly carbon-reducing polyester is equivalent to that of a polyester product prepared by an ethylene glycol prepared by a petrochemical method.

In some embodiments, the esterification catalyst is a mixture of zinc acetate, manganese acetate and lithium acetate.

In some embodiments, the weight of the esterification catalyst is 100-200 ppm of the weight of the polyethylene terephthalate.

In some embodiments, the amine stabilizer is selected from the group consisting of triethanolamine, triethylamine, tert-butylamine, diisopropylamine and combinations thereof; preferably triethanolamine.

In some embodiments, the phosphorus stabilizer is selected from the group consisting of triphenyl phosphite, triethyl phosphate, trimethyl phosphate, phosphoric acid, and combinations thereof.

In some embodiments, the molar ratio of zinc acetate, manganese acetate and lithium acetate in the mixture is 1:0.3-0.6:0.5-0.75; preferably 1:0.35-0.50:0.55-0.70, more preferably 1:0.40-0.45:0.55-0.60.

In some embodiments, the weight of the alcohol amine stabilizer is 35-50 ppm of the weight of the polyethylene terephthalate.

In some embodiments, the mass of the sodium bisulfite is 15-20 ppm of the mass of the polyethylene terephthalate.

In some embodiments, the mass of the phosphorus stabilizer is 125-150 ppm of the mass of the polyethylene terephthalate.

In some embodiments, the preparation method further comprises a step of adding a titanium-based multi-metal catalyst as a polymerization catalyst in the second esterification step.

Further, the titanium-based multi-metal catalyst can be the nano-supported solid-phase titanium-based multi-metal catalyst in CN117567730A, which is incorporated herein by reference in its entirety. By using the catalyst, the influence of low molecular byproducts in green EG on antimony catalysts such as ethylene glycol antimony can be avoided. The low molecular byproducts have reducing property, and can react with antimony catalysts to generate antimony precipitate, which reduces the catalytic activity of the catalyst, and cause poor hue and significantly reduced L value of the polyester product. The titanium-based multi-metal catalyst is a surface deposition solid-phase ultra-fine nanoporous catalyst, is coated with a surface silicon ester, has good dispersibility and maintains excellent stability in the polymerization process, wherein titanium is deposited on the surface of the carrier in the form of amorphous titanium dioxide, is firmly combined with the carrier, and part of the titanium dioxide is bonded to the surface of the carrier, thus having a mild catalytic effect and not forming titanium precipitate. Therefore, the hue of the chip of the obtained polyester is significantly improved, the L value of the polyester is significantly increased, and the polyester product quality is significantly better than that of the product using the antimony catalyst. The titanium-based multi-metal catalyst is an environmentally friendly catalyst, and can further improve the environmentally friendly level of the polyester product.

In some embodiments, the preparation method further comprises a step of adding a solid-phase tracer in the second esterification step; the solid-phase tracer is selected from the group consisting of hydrophilic nano-silica, gamma-nano-alumina, nano-barium sulfate powder, sub-nano composite calcium carbonate-magnesium carbonate, sub-nano attapulgite powder, and multi-element light metal zeolite nano-powder, and combinations thereof.

The green ethylene glycol of the present application is derived from industrial waste gas $CO_2$ capture and is used to prepare green ethylene glycol through an MTO process. However, in the present application process, the source of the green ethylene glycol cannot be indicated by chemical composition. Therefore, in order to accurately indicate the unique source of the green carbon capture ethylene glycol in the production and consumption links, the present application uses a tracer, that is, a chemically inert substance in the esterification, polymerization, spinning and consumption process, which can be accurately detected by instruments or chemical methods with a content of 20-300 ppm.

For the solid-phase tracer, an effective detection method is to determine the content of the marker by element emission spectrum, and to further confirm the presence of the nano marker by scanning electron microscope.

In some embodiments, the preparation method further comprises a step of adding a liquid-phase tracer to terephthalic acid and ethylene glycol before the first esterification step; the liquid-phase tracer is selected from the group consisting of isophthalic acid, phthalic acid, trimellitic acid, pyromellitic acid, cyclohexanedicarboxylic acid, 2,2,4,4-tetramethylcyclobutanedicarboxylic acid, pentaerythritol, neopentyl glycol, 1,2-dibutanol, 2,2,4,4-tetramethylcyclobutanediol, and 1,4-cyclohexanediol.

For the liquid-phase tracer, a polymerization monomer with obvious nuclear magnetic resonance effect is used, which can display absorption peaks of structural characteristics in the nuclear magnetic resonance region, and can be polymerized in the macromolecular chain segment as a monomer, and the content of the liquid-phase tracer is 50-300 ppm, which can display obvious absorption characteristic peaks in the nuclear magnetic resonance, and the liquid-phase marker can be combined with the solid-phase marker to comprehensively track and confirm the whole life cycle of the green ethylene glycol-based fiber.

Compared with the prior art, the present disclosure has the following advantages:

The present disclosure uses a novel catalyst with a columnar shape and a porous structure, and through a parallel multi-tower design of the first methanol reactor and a single or double tower design of the second methanol reactor, the equilibrium reaction of methanol synthesis can be promoted to move reversely to the positive reaction, and the conversion rate and selectivity of carbon dioxide in the synthesis of methanol from carbon dioxide are improved. The segmented reaction effectively prolongs the residence time of the mixed gas flow in the main reaction zone, and effectively improves the conversion rate of a single cycle reaction.

Figure 1:
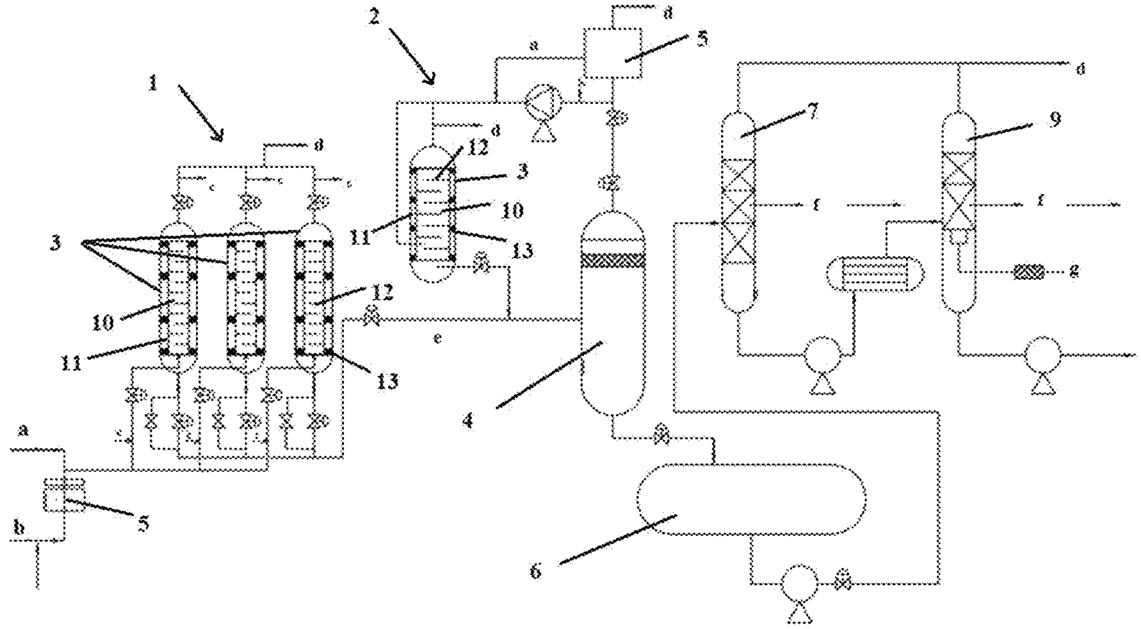
FIG. 1 is a schematic diagram of a methanol synthesis device used in the embodiment.

Wherein, 1—first-stage fixed bed reactor, 2—second-stage fixed bed reactor, 3—reaction tower, 4—methanol phase separation device, 5—pressure swing adsorption (PSA) device, 6—crude methanol storage tank, 7—low pressure methanol distillation tower, 9—medium pressure methanol distillation tower, 10—inner chamber, 11—outer chamber, 12—tray, 13—homogenizing disc, a—$H_2$, b—$CO_2$, c—$N_2$, d—tail gas, e—crude methanol+$CO_2$+$H_2$, f—refined methanol, g—fusel oil.

DETAILED DESCRIPTION

In the traditional synthesis of methanol by carbon dioxide hydrogenation reaction, for the high pressure and high temperature hydrogenation reactor, due to the limitation of material and reaction temperature (pressure resistance 15.0 Mpa, temperature resistance 350° C.), the structure volume of a single reactor can not be too large (generally according to the material balance, heat accounting and safety requirements, the full volume of 100,000 tons of methanol reactor is 50-100 $m^3$), so that the gas flow has a short residence time in the reactor. The existing methanol reactor design (the full volume of 100,000 tons of methanol reactor is about 50 $m^3$) adopts a large-flux self-circulation design of tail gas, which has high energy consumption, short residence time of mixed gas flow in the catalyst area, low single-pass reaction degree, and very low overall conversion rate of carbon dioxide.

In present disclosure, the first-stage methanol reactor adopts a parallel multi-tower single-circulation renewable catalyst design technology, the second-stage methanol reactor adopts a single/twin-tower design and a high-ratio self-circulation hydrogenation reaction, the reaction products at the bottom of the two-stage methanol reactors are introduced into a common methanol phase separation device after heat exchange and cooling, the crude methanol and the mixed gas not fully reacted are separated in the methanol phase separation device, the bottom crude methanol is introduced into a crude methanol intermediate tank, the top gas not fully reacted is compressed by a compressor and transported to the inner chamber at the bottom of the second-stage methanol reactor, so as to efficiently complete the preparation of methanol at a high ratio (3.6~6.0 times of circulation ratio).

The first-stage methanol reactor adopts a multi-tower design (for example, 3-6 independent reaction towers, one of which is a standby tower), which meets the needs of large capacity, single-circulation continuous operation, online regeneration or periodic replacement of catalyst, and in the running state, the effective capacity of each methanol reaction tower is 30,000-100,000 tons/year. The present disclosure adopts a multi-tower operation and one-tower standby operation process mode, and the actual operation capacity is 100,000-500,000 tons/year, and more methanol reaction towers can be further designed to improve the capacity.

The second-stage methanol reactor adopts a parallel double-tower structure design according to requirements, and in order to ensure long-period operation of the device, the second-stage methanol reactor adopts a one-tower operation and one-tower standby operation process mode, and catalyst regeneration and replacement can be conveniently completed. The second-stage methanol reactor needs to develop a catalyst with a hydrolysis-resistant effect, because the gas flow source contains a certain amount of moisture, the copper-zirconium-titanium-vanadium deposited hydrogenation catalyst (hydrolysis-resistant) does not contain an oxide component reacting with water, and the reaction temperature and pressure of the catalyst are different from those of the first-stage methanol reactor, the hydrogenation reaction can be completed at a lower temperature and a higher pressure, and the device operation period is greatly prolonged.

One of the aspects of the present disclosure is that a hydrolysis-resistant copper-zirconium-titanium-vanadium deposited hydrogenation catalyst is used in the second-stage methanol reactor, which has the effects of resisting hydrolysis and inactivation. The catalyst is developed and designed according to the characteristics of the reaction gas phase components separated by the methanol phase separation device after the reaction of the first-stage hydrogenation reactor is completed. By using the catalyst, the hydrogenation reaction can be completed at a lower temperature and a higher pressure, and the mixed phase is separated by gas-liquid separation, and then the crude methanol and high-boiling by-products are introduced into the crude methanol storage tank from the bottom of the reactor, and the gas phase part is guided out from the top of the reactor and sent into the third stage methanol reactor. In the second-stage reactor, by using the aforementioned hydrolysis-resistant hydrogenation catalyst, the carbon dioxide and hydrogen which are not reacted in the first-stage methanol reactor can further reacts so that the hydrogenation reaction degree of carbon dioxide is further improved.

Another of the aspects of the present disclosure is in the first-stage methanol reactor of the main reaction device, the raw material from a inlet is pure carbon dioxide and hydrogen mixed gas. Compared with the single stage designed methanol reactor, the unreacted recycled gas is injected into the mixed gas inlet in the present disclosure, and then the influence of the reaction by-products especially the water in the by-products on the catalyst activity is eliminated, the life of the hydrogenation catalyst is greatly prolonged, and the efficiency of the main reaction of the first-stage methanol reactor is improved. present disclosure One of the aspects of the present disclosure is the specific structural setting of the two-stage fixed bed reactor, specifically, the carbon dioxide gas and hydrogen are mixed after being compressed and injected into the system from the bottom of the inner chamber of the first-stage fixed bed reactor. The inner chamber of the reactor is designed as a multilayer tray design, for each stage of tray, the reaction mixed gas enters from a corner of the bottom of the tray, flows horizontally along the tray, and then enters the upper channel of the diagonal bottom corner into the upper tray, and so on to the top of the inner chamber. The design effectively prolongs the contact residence time of the mixed gas and the catalyst, and improves the reaction uniformity and reaction efficiency. The outer chamber is designed as a tower design, the mixed gas is collected to the top of the reactor after reacting in the inner chamber, and then enters the outer chamber to react, and the mixed gas flow in the outer chamber flows from the top to the bottom of the reactor and is collected, cooled by heat exchange, and introduced into the first methanol phase separation device. The top, middle and bottom of the outer chamber are all designed with multiple groups of homogenizing discs between which are filled with the catalyst particles. Each homogenizing disc first collects the gas, and then guides the gas to the next layer through the homogenizing design channel, so that the mixed gas flow uniformly passes through multiple catalyst layers in the tower body, and a filter screen is designed at the bottom of the outer chamber to prevent the catalyst particles from entering the bottom outlet.

One of the aspects of the present disclosure is that the first-stage methanol reactor adopts a multi-tower design, and each reaction tower can be isolated separately, and a high-temperature dry refined nitrogen gas inlet and outlet is arranged, after the catalyst in a single tower reaches the service cycle, it can be switched to a standby tower online, and then high-temperature (300-400° C.) nitrogen gas is used for purging. On the one hand, the catalyst adsorbed moisture can be dried. On the other hand, the coking of viscous by-products such as paraffin formed in the reaction process can be removed from the surface of the catalyst, and the catalyst regeneration is realized, and the service life of the catalyst is effectively extended, and the efficient reaction is always maintained through regular regeneration operation.

Different from ethylene glycol EG prepared by a petrochemical ethylene process, the green ethylene glycol prepared by the present disclosure has different impurity by-products in the composition, especially in the variety and content of low-molecular aldehydes and organic acids. In detail, the ethylene glycol prepared by the present disclosure has higher acetaldehyde content, lower 1,4-dioxane content, slightly higher low-molecular carboxylic acid content, and slightly lower ultraviolet light transmittance at 220 nm and 250 nm than the petrochemical ethylene glycol. This can lead to a decrease in the hue L value, a lower a value and a higher b value of the PET product. The esterification reaction rate of the green ethylene glycol is obviously lower than that of the petrochemical ethylene glycol, and under the same esterification conditions, the esterification conversion rate of the green ethylene glycol in the first esterification step is decreased by 3%-5%, and the esterification conversion rate of the green ethylene glycol in the second esterification step is decreased by 2.2%-4.0%.

One more of the aspects of the present disclosure is to add an esterification catalyst to ensure that the esterification reaction proceeds smoothly, the manganese element in the manganese acetate of the esterification catalyst has reducibility, and can react with a metal compound with oxidizability in the reaction process, and can also react with an oxidant component in the reaction system, thereby avoiding the deactivation of the effective active center components of antimony and titanium catalysts, and ensuring a good esterification reaction state of the green ethylene glycol. In addition, during polymerization, an alcohol amine stabilizer with complexing function is combined with sodium bisulfite to form a composite stabilizer with a phosphorus stabilizer. The alcohol amine stabilizer can effectively complex and block heavy metal ions and reducible low-molecular organic impurities in the green ethylene glycol, and the sodium bisulfite can block the by-products with active aldehyde and ketone groups, thereby reducing the side reaction level of the components, and the phosphorus stabilizer can control the thermal degradation reaction in the esterification and polymerization reaction processes.

The carbon dioxide hydrogenation for preparing methanol technology of the present disclosure adopts a parallel multi-tower (3-6 towers) renewable catalyst design for the first-stage methanol reactor, and a single/double-tower design for the second-stage methanol reactor, and the first-stage and second-stage methanol reactors share a methanol phase separation device, liquid-phase crude methanol is guided out from the bottom of the methanol phase separation device and sent to a crude methanol intermediate tank, and unreacted carbon dioxide and hydrogen and a by-product mixed gas are guided out from the top, the mixed gas is pressurized by a compressor and guided into the second-stage methanol reactor, and a self-circulation is designed in the second-stage methanol reactor, the methanol preparation is efficiently completed through high-ratio (3.6-6.0 circulation multiples) self-circulation. The full volume of the first-stage methanol reactor is effectively increased, and the residence time of a carbon dioxide and hydrogen mixed gas in the methanol reactor fixed bed is greatly increased by designing a large-capacity carbon dioxide hydrogenation reactor. The unique inner chamber gas phase flow channel design and outer chamber homogenization flow guide design make the reaction more uniform, and the first-stage methanol reactor does not adopt tail gas circulation, and the reaction conversion rate of the first-stage methanol reactor is increased. High-ratio self-circulation technology is used for the second-stage methanol reactor to further optimize the process, and the catalyst service cycle is prolonged by using a more reasonable process, and the conversion efficiency is increased, and the device operation stability is further increased.

The present disclosure is further explained in detail below in combination with specific embodiments; it should be understood that, those embodiments are to explain the basic principle, major features and advantages of the present disclosure, and the present disclosure is not limited by the scope of the following embodiments; the implementation conditions employed by the embodiments may be further adjusted according to particular requirements, and undefined implementation conditions usually are conditions in conventional experiments. In the following embodiments, unless otherwise specified, all raw materials are basically commercially available or prepared by conventional methods in the field.

The embodiments described below are only for illustrating the technical concepts and features of the present disclosure, and are intended to make a person familiar with the technology being able to understand the content of the present disclosure and thereby implement it, and should not limit the protective scope of this disclosure. Any equivalent variations or modifications according to the spirit of the present disclosure should be covered by the protective scope of the present disclosure.

The present application is further described below in combination with the drawings and the preferred embodiments of the present application. The orientation and position relationship described in the present application are only for the convenience of description and simplifying the description, and are not used to indicate or imply that the device or element referred to must have a specific orientation, only have a specific orientation, be constructed and operated in a specific orientation, and therefore cannot be understood as a limitation on the present application.

Figure 2:
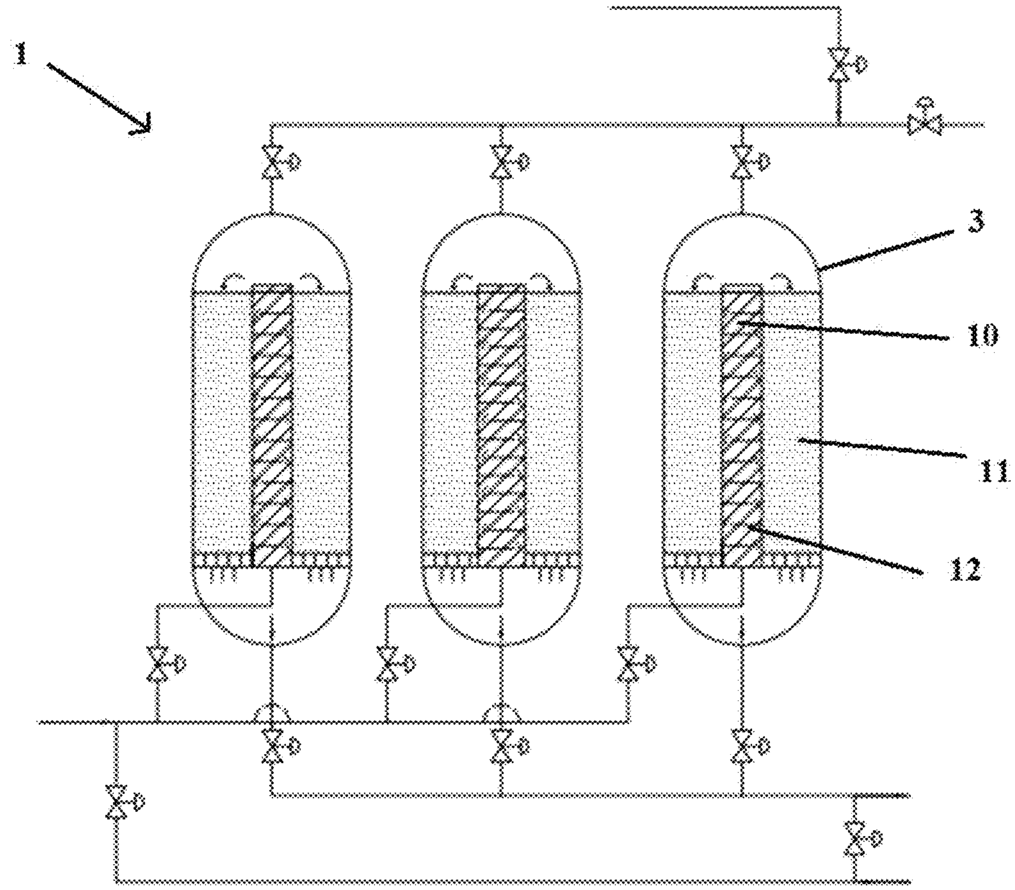
FIG. 2 is a schematic diagram of a first-stage fixed bed reactor used in the embodiment.

As shown in FIG. 1 and FIG. 2, the device system for preparing methanol comprises two-stage fixed bed reactors for synthesizing methanol in FIG. 1, wherein the first-stage fixed bed reactor is enlarged as shown in FIG. 2. The first-stage fixed bed reactor 1 is filled with a copper-zinc-calcium-magnesium-aluminum hydrogenation catalyst, and the second-stage fixed bed reactor 2 is filled with a copper-zirconium-titanium-vanadium deposition hydrogenation catalyst.

As shown in FIG. 1 and FIG. 2, both of the first-stage fixed bed reactor 1 and the second-stage fixed bed reactor 2 comprise an inner chamber 10 and an outer chamber 11. The inner chamber 10 comprises multiple layers of horizontally arranged trays 12 and two adjacent trays 12 are staggered. The outer chamber 11 is designed in a tower type, and multiple groups of homogenizing trays 13 are arranged at the top, middle and bottom of the outer chamber 11. The copper-zinc-calcium-magnesium-aluminum hydrogenation catalyst is filled between the homogenizing trays 13 of the inner chamber 10 and the outer chamber 11. A filter screen (not shown in the figure) is arranged at the bottom of the outer chamber 11.

As shown in FIG. 1, carbon dioxide and hydrogen are mixed and pressurized, and then fed from the bottom into the first-stage fixed bed reactor 1 for hydrogenation reaction. The gas stream after reaction flows out from the bottom of the first-stage fixed bed reactor 1, enters a condenser for condensation, and then enters the first methanol phase separation device 4 for phase separation after depressurization. The gas stream at the top of the first methanol phase separation device 4 is mixed with additional hydrogen, and then pressurized and fed from the middle and lower part into the second-stage fixed bed reactor 2. The mixed gas stream is subjected to hydrogenation reaction in the second-stage fixed bed reactor 2. The liquid components after reaction flow out from the bottom of the second-stage fixed bed reactor 2, and enter the first methanol phase separation device 4 for phase separation. The tail gas at the top of the second-stage fixed bed reactor 2 is subjected to depressurization treatment, and then led into the pressure swing adsorption (PSA) device 5 for hydrogen adsorption, desorption and recovery. The recovered hydrogen is used as the additional hydrogen fed into the second-stage fixed bed reactor 2. The liquefied crude methanol obtained from the two-stage fixed bed reactors and methanol phase separation device 4 can be stored in the crude methanol storage tank 6.

As shown in FIG. 1, the liquid crude methanol obtained from the methanol phase separation device 4 is subjected to two-stage distillation separation. The pressure of the second-stage distillation is higher than that of the first-stage distillation. For the two-stage distillation separation system, the first-stage distillation adopts low pressure distillation. The crude methanol is fed into the bottom of the low pressure methanol rectification tower 7. The methanol is taken out from the top of the distillation tower, cooled and returned to the refined methanol storage tank 10. The heavy components at the bottom of the low pressure methanol distillation tower 7 mainly include 50%-60% methanol and other high boiling point by-products, which are fed into the middle of the medium pressure methanol distillation tower 9 by a circulating pump, and then high quality methanol is further taken out from the top of the tower by distillation, cooled and returned to the refined methanol storage tank. The high boiling point components taken out from the bottom are fed into the fusel oil storage tank as fusel oil for further treatment.

Preparation Example 1

The present preparation example provides a copper-zinc-calcium-magnesium-aluminum hydrogenation catalyst, and a preparation method thereof is specifically as follows:

First, 1.0M of aqueous solutions of a copper sulfate, zinc sulfate, calcium chloride, magnesium sulfate, aluminum sulfate are prepared respectively and filtered for use. 1.0M sodium hydroxide solution, 0.5M sodium bicarbonate solution is also prepared. A zinc sulfate solution, magnesium sulfate solution, aluminum sulfate solution is mixed in a molar ratio of 1.0:1.0:0.75 to obtain a mixed solution, and the sodium hydroxide solution is added dropwise into the mixed solution under stirring in 4.0 hours, with the molar ratio of metal ions and hydroxide in accordance with the stoichiometric ratio, and a co-precipitation deposition suspension is obtained. The temperature of the reaction system is controlled at 70° C., and after the drop addition is completed, the reaction is continued for 2.0 hours.

A copper sulfate solution, calcium chloride solution in a molar ratio of 1.5:1.8 and the sodium hydroxide solution are added dropwise to the co-precipitation deposition suspension simultaneously and the total valence of the two metal ions was equal to the total valence of hydroxide ions, and the dropwise addition time is controlled for 4 hours, and the pH value of the system is controlled at about 10 during the dropwise addition. After the completion of the dropwise addition, the pH value of the suspension is adjusted to 10.0 with the sodium bicarbonate solution. The suspension is heated to 90° C. and stabilized for 1.0 hour. Then the suspension is transferred to a 2.5 MPa pressure-resistant stainless steel reactor, heated to 220° C. under high-speed stirring conditions and stirred for 5.0 hours, and then a high-pressure circulating pump is started, and the suspension is transported to a specially designed high-pressure blasting nozzle. The suspension is first dehydrated under high-pressure overheating conditions in the high-pressure blasting nozzle, and then suddenly blasted to normal pressure conditions, and in the process, the submicron powder in the suspension is blasted into nano powder, and the porosity and specific surface area of the powder are greatly improved.

The nano powder after blasting is partially dehydrated, the soluble components are washed away with distilled water, and then a water suspension with a concentration of 10% is formed under stirring. Tetrabutyl silicate accounting for 150 ppm of the powder mass is added dropwise to the water suspension at 80° C., and the dropwise addition time is controlled for 6 hours, after the completion of the dropwise addition, aging is performed for 2.0 hours. The water is removed by filtration, and submicron graphite, coconut shell carbon micro powder and a binder (the mass ratio of the three is 3:5:2) are added to the filter cake as a supporting carrier to prepare columnar porous pellets, which are dried and shaped at 320° C. to obtain a copper-zinc-calcium-magnesium-aluminum hydrogenation catalyst.

The specific surface area of the catalyst is 125 $m^2/g$, and the catalyst is columnar with a length of 4.0 mm.

In the catalyst, the supporting carrier accounts for 40 wt %, and the active component accounts for 60 wt %. In the active component, a copper oxide accounts for 35.0 wt %, a zinc oxide accounts for 26.0 wt %, a calcium oxide accounts for 4.2 wt %, a magnesium oxide accounts for 16.8 wt %, and a aluminum oxide accounts for 18.0 wt %.

Preparation Example 2

The present preparation example provides a copper-zirconium-titanium-vanadium deposition hydrogenation catalyst, and a preparation method thereof is specifically as follows:

A prepared copper sulfate aqueous solution (concentration: 3.0 mol/L), tetraethyl zirconium, tetraisopropyl titanate, sodium metavanadate aqueous solution (concentration: 2.0 mol/L), sodium hydroxide aqueous solution (concentration: 2.5 mol/L), and sodium carbonate aqueous solution (concentration: 2.0 mol/L) are synchronously added dropwise into a nano-silica which used as a carrier. The pH value of the system is strictly controlled to be 10 during the dropwise addition. The precipitates formed by the reaction of the four metal ions with the alkali liquor are deposited on the surface of the nano-silica carrier to form a porous deposition catalyst layer. Then, the suspension is filtered and washed, and is mixed with submicron graphite, coconut shell carbon micro powder and a binder (mass ratio: 3:5:2, as a supporting carrier) to be compressed into columnar porous catalyst particles. The columnar porous catalyst particles are sent into a muffle furnace for treatment at 600° C. for 16 hours to obtain a copper-zirconium-titanium-vanadium deposition hydrogenation catalyst. The surface of the catalyst is porous.

The specific surface area of the catalyst is 100 $m^2/g$, and the catalyst is columnar with a length of 5.0 mm.

In the catalyst, the supporting carrier accounts for 40 wt %, the nano-silica carrier accounts for 20 wt %, and the active component porous deposition catalyst layer accounts for 40 wt %. In the active component, the copper oxide accounts for 45 wt %, the zirconium oxide accounts for 30 wt %, the titanium oxide accounts for 12.0 wt %, and the vanadium oxide accounts for 13.0 wt %.

Comparative Preparation Example 1

A hydrogenation catalyst is prepared by the method as in Preparation Example 1, by only differing in that: the raw materials don't comprise calcium chloride aqueous solution.

Comparative Preparation Example 2

A hydrogenation catalyst is prepared by the method as in Preparation Example 1, by only differing in that: the raw materials don't comprise the magnesium sulfate aqueous solution.

Comparative Preparation Example 3

A deposition hydrogenation catalyst is prepared by the method as in Preparation Example 2, by only differing in that: the raw materials don't comprise the tetraethyl zirconium.

Comparative Preparation Example 4

A deposition hydrogenation catalyst is prepared by the method as in Preparation Example 2, by only differing in that: the raw materials does not comprise the sodium metavanadate aqueous solution.

Example 1

This example provides a preparation method of methanol, and the method is specifically as follows.

Taking a 500,000 t/year methanol device prepared by hydrogenation of carbon dioxide as an example, the sources and quality indexes of raw hydrogen and carbon dioxide are as follows:

Hydrogen: when propylene is prepared by a methanol-to-olefin technology (MTO process) with green power as energy, the byproduct is hydrogen. The quality indexes (hydrogen content and impurity content) and process parameter are as shown in Table 1 below:

TABLE 1 hydrogen raw material indexes and process parameters

| Gas component, process parameter | Component content (volume), process parameter |
|---|---|
| $H_2$ | ≥99.99% (VOL) |
| $O_2$ | ≤5 ppm |
| CO | ≤1 ppm |
| $CO_2$ | ≤10 ppm |
| $H_2O$ | ≤50 ppm |
| $CH_4$ | ≤50 ppm |
| $C_2H_4$ | ≤10 ppm |
| $C_3H_6$ | ≤10 ppm |
| $H_2S$ | ≤1 ppm |
| $N_2$ | ≤100 ppm |
| Temperature | 42° C. |
| Pressure | 2.4 MPa |
| Flow rate | 137800 $Nm^3/h$ ($Nm^3$/hour) |

Carbon dioxide: The high concentration carbon dioxide gas stream (mass index shown in Table 2 below) generated in petroleum refining is recovered. The carbon dioxide waste gas is first captured, compressed, enriched (by pressure swing adsorption PSA device), desulfurized and denitrified to prepare carbon dioxide raw gas with a volume content of more than 98.0%;

TABLE 2 carbon dioxide raw material index and process parameters

| Gas component, process parameter | Component content (volume), process parameter |
|---|---|
| $CO_2$ | 80.0-92% vol |
| $H_2$ | ≤0.16% vol |
| $H_2O$ | Saturated |
| $N_2$ | 15.0-19.98% vol |
| CO | ≤0.01% vol |
| Temperature | 40° C. |
| Pressure | 0.5 MPa |
| Flow rate | 47200 $Nm^3/h$ ($Nm^3$/hour) |

The purified carbon dioxide gas is mixed with hydrogen, and then pressurized to 10.0 MPa and heated to 265° C. The mixed gas is delivered to the inner chamber of the first-stage methanol reactor (first-stage fixed bed reactor), flows through the catalyst fixed bed in the inner chamber, and then reaches the top of the methanol reactor. The mixed gas flows uniformly from top to bottom through the outer chamber homogenizer at the top, the outer chamber multilayer catalyst fixed bed and the gas homogenizer to complete the first-stage circulating process catalytic hydrogenation reaction. The mixed gas is delivered from the bottom of the outer chamber to the first methanol phase separation device through heat exchange and pressure reduction equipment. The catalysts filled in the inner chamber and the outer chamber are the catalysts of Preparation Example 1. In the first-stage methanol reactor, the total residence time of the carbon dioxide and hydrogen mixed phase is 310 seconds. The results are that the carbon dioxide conversion rate is 72.80% and the reaction selectivity is more than 97.0%.

The methanol phase separation device is further cooled and refluxed, and heavy components such as crude methanol and reaction generated water are collected from the bottom and then delivered to a crude methanol intermediate tank.

The mixed gas that is not reacted at the top of the methanol phase separation device is pressurized and heated (the temperature is raised to 180° C. and the pressure is raised to 15.0 MPa) by a compressor and a heat exchanger, and then delivered to the second-stage methanol reactor (second-stage fixed bed reactor). The second-stage methanol reactor adopts a design structure different from that of the first-stage reactor, and the gas-liquid phase unreacted mixed gas, crude methanol, water and high boiling point by-products are led out from the bottom and delivered to the first methanol phase separation device for separation.

The mixed gas at the top of the methanol phase separation device which is from the first and second methanol reactors is recycled to the second methanol reactor via a compressor. The main gas in the gas phase at the top of the methanol phase separation device is compressed and subjected to high-rate self-circulation (3.6-6.0), and the remaining gas is sent to a PSA hydrogen recovery device in a controlled small flow, concentrated and introduced into a inlet of a second-stage mixed gas circulating compressor for reuse, and a tail gas is sent to a tail gas incineration device for harmless emission.

The second methanol reactor is filled with the catalyst prepared in the preparation example 2. The residence time of the mixed phase in the second methanol reactor is 80 seconds, and the effective self-circulation ratio is 3.5 times. After the second methanol reactor, the cumulative conversion rate of carbon dioxide is 95.12%.

The crude methanol taken out from the first and second methanol reactors is collected into a crude methanol storage tank and then sent to a two-stage distillation system. A refined methanol is taken out from the top of a first-stage low-pressure methanol distillation tower, and methanol, water and high-boiling by-products are taken out from the bottom. The components are heated and gasified and sent to a second-stage medium-pressure distillation tower. After the two-stage distillation tower, refined methanol is taken out from the top, and heavy components at the bottom are refluxed to separate water which is then sent to a water treatment device for treatment. The remaining fusel oil after water removal is sent to a fusel oil storage tank for storage and treatment. The tail gas is collected into a tail gas treatment device, treated and vented. The refined methanol products distilled from the two-stage distillation towers are collected into a refined methanol storage tank. The indexes of refined methanol product are shown in Table 3.

TABLE 3

| Methanol product indexes (GB 338-2011) | |
|---|---|
| Item | GB 338-2011 (superior) |
| Appearance | Colorless and transparent, no visible impurities |
| Methanol content | ≥99.85% w/w |
| Acetone | — |
| Acid (calculated as HCOOH) | ≤0.0015% w/w |
| Carbonizable substances (sulfuric acid washing test, platinum-cobalt color number) | ≤50 |
| Chroma | ≤5 |
| Boiling range 760 mm | ≤0.8° C. |
| Evaporation residue | ≤0.001% w/w |
| Odor | No abnormal odor |
| Potassium permanganate test | ≥50 min |
| Specific gravity at 20° C. | 0.791-0.792 g/cm$^3$ |
| Moisture | ≤0.10% w/w |
| Hydroxy compounds (as HCHO) | ≤0.002% w/w |

For the 500,000 t/year carbon dioxide hydrogenation to prepare methanol project of the present embodiment, the carbon dioxide conversion rate was 94.88%, and the device material balance data are as shown in Table 4.

TABLE 4

Project process device material balance table

| Project name | Material name | Unit | Value |
|---|---|---|---|
| Feed | $H_2$ feed gas | Kg/h | 12435 |
| | $CO_2$ feed gas | Kg/h | 92160 |
| Output product | Refined methanol | Kg/h | 62320 |
| | By-product water | Kg/h | 35510 |
| | Tail gas | Kg/h | 6035 |
| | Fusel oil | Kg/h | 725 |

Comparative Example 1

The present comparative example provides a method for preparing methanol, which is basically the same as that of Example 1, by only differing in that: the catalysts in the first-stage fixed bed reactor and the third-stage fixed bed reactor are replaced with the catalyst of Comparative Preparation Example 1. As a result, the cumulative conversion rate of carbon dioxide is 91.35%.

Comparative Example 2

The present comparative example provides a method for preparing methanol, which is basically the same as that of Example 1, by only differing in that: the catalysts in the first-stage fixed bed reactor and the third-stage fixed bed reactor are replaced with the catalyst of Comparative Preparation Example 2. As a result, the cumulative conversion rate of carbon dioxide is 90.82%.

Comparative Example 3

The present comparative example provides a method for preparing methanol, which is basically the same as that of Example 1, by only differing in that: the catalyst in the second-stage fixed bed reactor is replaced with the catalyst of Comparative Preparation Example 3. As a result, the cumulative conversion rate of carbon dioxide is 89.53%.

Comparative Example 4

The present comparative example provides a method for preparing methanol, which is basically the same as that of Example 1, by only differing in that: the catalyst in the second-stage fixed bed reactor is replaced with the catalyst of Comparative Preparation Example 4. As a result, the cumulative conversion rate of carbon dioxide is 88.76%.

Example 2

The present example provides a method for preparing green ethylene glycol, which is specifically as follows:

The green refined methanol prepared in Example 1 is transported to an MTO device for preparing olefins from methanol, in which the green refined methanol is first used to prepare ethylene, and then the ethylene is used to prepare green ethylene oxide by oxidation, and the green ethylene oxide is hydrolyzed to prepare green ethylene glycol. The process for preparing green ethylene glycol from green methanol has been widely applied in the methanol chemical industry, and the present example adopts a conventional chemical industry implementation mode. The indexes of the finally obtained green ethylene glycol are shown in Table 5.

The obtained green ethylene glycol meets the requirements of GB/T4649-2018 and conforms to the quality requirements of polyester-grade ethylene glycol raw materials, but compared with petrochemical ethylene glycol, the tested ultraviolet transmittance at 220 nm and 250 nm of it is lower than that of petrochemical ethylene glycol, although it meets the national standard quality requirements. The reason is that the content of low-molecular aldehydes, carboxylic acids and low-molecular carboxylic acid esters, and alcohol by-products in the green ethylene glycol is higher than that in the petrochemical ethylene glycol.

TABLE 5 performance indicators of green ethylene glycol

| No. | Item | Standard requirement of polyester-grade ethylene glycol | Performance of EG of Example 2 | Note: |
|---|---|---|---|---|
| 1 | Appearance | Transparent liquid, no mechanical impurities | Transparent liquid, no mechanical impurities | |
| 2 | Ethylene glycol, w % ≥ | 99.9 | 99.95 | |
| 3 | Diethylene glycol, w % ≤ | 0.050 | 0.016 | |
| 4 | 1,4-Butanediol [a], w % | Reported [b] | 0.004 | Reported [b] |
| 5 | 1,2-Butanediol [a], w % | Reported [b] | 0.001 | Reported [b] |
| 6 | 1,2-Hexanediol [a], w % | Reported [b] | Not detected | Reported [b] |
| 7 | Ethylene carbonate [a], w % | Reported [b] | 0.002 | Reported [b] |
| 8 | Chromaticity (platinum-cobalt)/number Before heating ≤<br>After heating with hydrochloric acid ≤ | 5<br>20 | 1.2<br>6.3 | |
| 9 | Density (20° C.) (g/cm$^3$) | 1.1128~1.1138 | 1.1132 | |
| 10 | Boiling range (at 0° C., 101.33 Kpa)<br>Initial boiling point/° C. ≥<br>Dry point/° C. ≤ | 196.0<br>199.0 | 196.4<br>198.6 | |
| 11 | Moisture, w % ≤ | 0.08 | 0.06 | |
| 12 | Acidity (calculated as acetic acid)/(mg/kg) ≤ | 10 | 4.2 | |
| 13 | Iron content/(mg/kg) ≤ | 0.10 | 0.01 | |
| 14 | Ash/(mg/kg) ≤ | 10 | 0.8 | |
| 15 | Aldehyde content(calculated as formaldehyde)/(mg/kg) ≤ | 8.0 | 6.2 | |
| 16 | Ultraviolet transmittance/%<br>220 nm ≥<br>250 nm<br>275 nm ≥<br>350 nm ≥ | 75<br>Reported [b]<br>92<br>99 | 77.9<br>Reported [b]<br>93.4<br>99.9 | Compared with the ethylene glycol obtained by the petrochemical method, the measured values of 220 nm and 250 nm are slightly low |
| 17 | Chloride ion/(mg/kg) ≤ | 0.5 | 0.02 | |

[a] The petrochemical method and the ethylene oxidation/ethylene oxide hydration process do not require the item, but the green method requires the item

[b] "Reported" means that the data need to be measured and provided, and items 4-7 in the above table are given according to a report Example 3

The present example provides a preparation method for green polyethylene terephthalate (PET), which is specifically as follows.

The green ethylene glycol prepared in the above example 2 is used as a raw material of polyester, and polymerization and spinning is performed on a 50,000 t/year continuous polymerization melt direct spinning device.

Device capacity: 150t/d, using ultra-low temperature five-kettle process design, and by melt direct spinning.

A refined terephthalic acid (PTA) and the green ethylene glycol (EG) are configured into slurry in a molar ratio of 1:1.135, and a prepared esterification catalyst, namely, a mixture of zinc acetate, manganese acetate and lithium acetate (molar ratio of 1:0.3:0.5) is injected into a slurry tank, and the total addition amount of the esterification catalyst is controlled to be 100 ppm of polyester product PET. A composite stabilizer is injected into the slurry through a designed injection port in a slurry conveying pipeline, and the composite stabilizer is consisted of triethanolamine, sodium bisulfite and triphenyl phosphite, wherein the amount of the triethanolamine accounts for 50 ppm of the mass of PET, the amount of the sodium bisulfite accounts for 20 ppm of the mass of PET, and the amount of the triphenyl phosphite accounts for 150 ppm of the mass of PET.

After the slurry is uniformly mixed, the slurry is conveyed to a first esterification reactor for a preliminary esterification reaction, and the temperature of the first esterification reactor is controlled to be 256-258° C., the pressure is controlled to be 75 KPa, and the esterification rate of the first esterification reactor is controlled to be 90%-91.5%.

The melt after the reaction in the first esterification reactor is introduced into the second esterification reactor. The second esterification reactor is a multi-chamber design and is divided into three esterification reaction chambers. The reaction temperature at the outlet of the second esterification reactor is 260-262° C. A prepared nano-barium sulfate tracer (a suspension of barium sulfate in ethylene glycol, the mass concentration is 5%, and the particle size of the barium sulfate is 50 nm) is added into the first chamber of the second esterification reactor. The amount of the nano-barium sulfate tracer is 50 ppm of the mass of PET, and the nano-barium sulfate tracer is used as a marker to track the whole life cycle of the green carbon-reduced polyester. A titanium-based multi-metal catalyst (the catalyst in Example 1 of CN117567730A) is added into the second chamber of the second esterification reactor. The concentration of titanium element is 8 ppm of the mass of PET. A liquid matting agent is added into the third chamber of the second esterification reactor. The mass of the liquid matting agent is 0.3% of the mass of PET.

The melt after the second esterification reaction in the second esterification reactor is introduced into a first prepolymerization reactor. The esterification rate of the melt is 96.5%-97.8%. The reaction temperature in the first prepolymerization reactor is controlled to be 269-271° C. The vacuum degree is 10.0-12.0 KPa. The melt after a first prepolymerization reaction in the first prepolymerization reactor is introduced into a second prepolymerization reactor to further complete the prepolymerization reaction. The second prepolymerization reactor is a single-shaft disc reactor. The reaction temperature is controlled to be 273-275° C. The vacuum degree is 1.0-1.3 KPa. The intrinsic viscosity of the prepolymer is controlled to be 0.240-0.285 (measured in a mixed solvent of phenol:tetrachloroethane=3:2 (V/V)). The melt after the prepolymerization reaction is conveyed to the final polymerization reactor through a prepolymer conveying pump and a prepolymer filter. The final polymerization reactor is a front-rear double-shaft disc reactor. The reaction temperature at the outlet of the final polymerization reactor is controlled to be 280-282° C. The vacuum degree is 150-175 Pa. The intrinsic viscosity at the outlet is controlled to be 0.640-0.645 (measured in a mixed solvent of phenol:tetrachloroethane=3:2 (V/V)). The melt is conveyed to a direct spinning workshop through a melt conveying pump. Various green carbon-reduced polyester fibers with different specifications are spun. The process parameters are shown in Table 6.

Example 4

The present example provides a method for preparing green polyethylene terephthalate PET, which is basically the same as that of Example 3, by only differing in that: the process parameters are slightly different and as shown in Table 6 below, and the dosage of the tracer barium sulfate added into the first chamber of the second esterification reactor is increased to 100 ppm.

Example 5

The present example provides a method for preparing green polyethylene terephthalate PET, which is basically the same as that of Example 3, by only differing in that: the process parameters are slightly different and as shown in Table 6 below, and 60 ppm (based on mass of PET) of 2,2,4,4-cyclohexanedicarboxylic acid is added into the pulping reactor and 50 ppm (based on mass of PET) of nano-barium sulfate is also added into the second esterification reactor.

Example 6

The present example provides a method for preparing green polyethylene terephthalate PET, which is basically the same as that of Example 3, by only differing in that: the process parameters are slightly different and as shown in Table 6 below, and 80 ppm (based on mass of PET) of 2,2,4,4-cyclohexanedicarboxylic acid is added into the pulping reactor and 80 ppm (based on mass of PET) of nano-barium sulfate is added into the second esterification reactor.

Example 7

The present example provides a method for preparing green polyethylene terephthalate PET, which is basically the same as that of Example 3, by only differing in that: the process parameters are slightly different and as shown in Table 6 below, and 75 ppm (based on mass of PET) of 2,2,4,4-cyclohexanedicarboxylic acid is added into the pulping reactor and 100 ppm (based on mass of PET) of sub-nanometer calcium carbonate-magnesium carbonate composite (calcium: 40 ppm, magnesium: 60 ppm) is added into the second esterification reactor.

Example 8

The present example provides a method for preparing green polyethylene terephthalate PET, which is basically the same as that of Example 3, by only differing in that: the process parameters are slightly different and as shown in Table 6 below, and 75 ppm (based on mass of PET) of pentaerythritol is added into the pulping reactor and 100 ppm (based on mass of PET) of sub-nanometer calcium carbonate-magnesium carbonate composite (calcium: 40 ppm, magnesium: 60 ppm) is added into the second esterification reactor.

TABLE 6

| Process parameters | | | | | | | | | |
|---|---|---|---|---|---|---|---|---|---|
| No. | First esterification (° C./kpa) | First esterification acid value/mgKOH/t | Second esterification (° C.) | Second esterification acid value/ mgKOH/t | First prepolymeri-zation (° C./kpa) | Second prepolymeri-zation (° C./kpa) | Prepolymer viscosity | Final polymeri-zation (° C./pa) | Outlet intrinsic viscosity |
| Example 3 | 255.8/75.0 | 67.8 | 262.0 | 28.9 | 270.5/10.1 | 273.4/1.03 | 0.267 | 281.5/155.0 | 0.643 |
| Example 4 | 256.0/75.0 | 68.2 | 262.3 | 28.2 | 270.8/10.0 | 273.5/1.03 | 0.265 | 281.2/153.0 | 0.641 |
| Example 5 | 255.6/75.0 | 69.7 | 262.9 | 28.8 | 270.3/10.6 | 273.9/1.02 | 0.269 | 281.9/158.7 | 0.644 |
| Example 6 | 256.3/75.0 | 66.6 | 262.1 | 27.1 | 271.4/10.2 | 274.2/1.12 | 0.270 | 280.9/159.5 | 0.645 |
| Example 7 | 257.5/75.0 | 67.7 | 262.5 | 28.6 | 270.5/10.3 | 273.4/1.04 | 0.272 | 281.7/156.4 | 0.642 |
| Example 8 | 257.3/75.0 | 64.7 | 263.2 | 26.9 | 270.6/10.0 | 273.8/1.02 | 0.275 | 282.2/160.3 | 0.643 |
| Comparative Example 1 | 256.5/75.0 | 73.8 | 262.3 | 31.3 | 272.6/10.6 | 274.8/1.05 | 0.286 | 283.5/155.2 | 0.644 |
| Comparative Example 2 | 256.3/75.0 | 65.5 | 262.5 | 23.5 | 272.7/10.4 | 275.6/1.16 | 0.289 | 283.1/158.0 | 0.647 |
| Comparative Example 3 | 256.7/75.0 | 73.7 | 262.8 | 31.2 | 273.2/10.2 | 274.6/1.16 | 0.284 | 283.2/165.3 | 0.643 |
| Comparative Example 4 | 256.2/75.0 | 71.2 | 262.9 | 29.5 | 272.9/10.3 | 274.7/1.11 | 0.286 | 283.2/155.0 | 0.645 |

Note:
Intrinsic viscosity is measured in a mixed solvent of phenol:tetrachloroethane = 3:2 (V/V)

Comparative Example 5

The present comparative example provides a method for preparing PET, which is basically the same as that of Example 3, by only differing in that: no esterification catalyst, tracer, and composite stabilizer were added.

Comparative Example 6

The present comparative example provides a method for preparing PET, which is basically the same as that of Example 3, by only differing in that: the esterification catalyst was added, while no tracer and composite stabilizer were added.

Comparative Example 7

The present comparative example provides a method for preparing PET, which is basically the same as that of Example 3, by only differing in that: a ethylene glycol antimony catalyst was used, while no tracer, esterification catalyst, and composite stabilizer were added.

Comparative Example 8

The present comparative example provides a method for preparing PET, which is basically the same as that of Example 3, by only differing in that: the polymerization monomers were EG and PTA obtained by the petrochemical method, and a ethylene glycol antimony catalyst was used, while no tracer, esterification catalyst, and composite stabilizer were added.

The use of each additive agent is shown in Table 7 below.

TABLE 7

| Additive agent using | | | | | | | |
|---|---|---|---|---|---|---|---|
| No. | Stabilizer 1 Triethanolamine | Stabilizer 2 Sodium bisulfite | Stabilizer 3 Triphenyl phosphite | Esterification catalyst (zinc acetate, lithium acetate, manganese acetate) | Tracer 1 (qualitative) | Tracer 2 Solid phase (qualitative) | Polymerization catalyst (titanium series) |
| Example 3 | 35 ppm | 15 ppm | 135 ppm | 110 ppm | 0 | 50 ppm | 8 ppm |
| Example 4 | 35 ppm | 15 ppm | 135 ppm | 110 ppm | 0 | 100 ppm | 8 ppm |
| Example 5 | 35 ppm | 15 ppm | 135 ppm | 110 ppm | 60 ppm | 50 ppm | 8 ppm |
| Example 6 | 35 ppm | 15 ppm | 135 ppm | 110 ppm | 80 ppm | 80 ppm | 8 ppm |
| Example 7 | 35 ppm | 15 ppm | 135 ppm | 110 ppm | 75 ppm | 100 ppm* | 8 ppm |
| Example 8 | 35 ppm | 15 ppm | 135 ppm | 110 ppm | 75 ppm* | 100 ppm* | 8 ppm |
| Comparative Example 5 | | | | | | | 8 ppm |
| Comparative Example 6 | | | | 110 ppm | | | 8 ppm |
| Comparative Example 7 | | | | | | | 210 ppmSb |

TABLE 7-continued

| Additive agent using | | | | | | | |
|---|---|---|---|---|---|---|---|
| No. | Stabilizer 1 Triethanolamine | Stabilizer 2 Sodium bisulfite | Stabilizer 3 Triphenyl phosphite | Esterification catalyst (zinc acetate, lithium acetate, manganese acetate) | Tracer 1 (qualitative) | Tracer 2 Solid phase (qualitative) | Polymerization catalyst (titanium series) |
| Comparative Example 8 | | | | | | | 210 ppmSb |

Note:
Tracer 1: 2,2,4,4-tetramethylcyclobutanedicarboxylic acid,
*pentaerythritol; Tracer 2: nano barium sulfate,
*sub-nanometer composite calcium carbonate-magnesium carbonate (calcium: 40 ppm, magnesium: 60 ppm, total: 100 ppm)

The semi-dull PET polyester prepared in each of the above examples and comparative examples was tested for performance, and the results are shown in Table 8 below, wherein the intrinsic viscosity was measured in a mixed solvent of phenol and tetrachloroethane (3:2 V/V).

TABLE 8

| Performance of semi-dull PET polyester | | | | | | | | |
|---|---|---|---|---|---|---|---|---|
| No. | Intrinsic viscosity(dl/g) 3:2 | Melting point° C. | DEG content (%) | End carboxyl content (mgKOH/Kg) | Hue L value | Hue B value | dulling agent content (%) | Ash content (%) |
| Example 3 | 0.643 | 258.2 | 1.29 | 27.7 | 81.0 | 3.8 | 0.300 | 0.0 |
| Example 4 | 0.641 | 258.5 | 1.30 | 28.2 | 80.8 | 3.6 | 0.300 | 0.0 |
| Example 5 | 0.644 | 258.0 | 1.32 | 27.4 | 81.2 | 3.9 | 0.299 | 0.0 |
| Example 6 | 0.645 | 258.3 | 1.28 | 28.7 | 79.9 | 4.1 | 0.301 | 0.1 |
| Example 7 | 0.642 | 257.6 | 1.26 | 29.2 | 80.7 | 3.4 | 0.297 | 0.0 |
| Example 8 | 0.643 | 258.0 | 1.30 | 27.6 | 81.2 | 3.7 | 0.297 | 0.0 |
| Example 5 | 0.647 | 257.4 | 1.33 | 33.0 | 78.8 | 6.8 | 0.303 | 0.0 |
| Example 6 | 0.643 | 257.5 | 1.31 | 27.7 | 79.0 | 7.2 | 0.300 | 0.1 |
| Example 7 | 0.645 | 257.9 | 1.29 | 34.1 | 78.6 | 5.9 | 0.299 | 0.0 |
| Example 8 | 0.643 | 259.2 | 1.28 | 28.8 | 83.7 | 2.8 | 0.300 | 0.0 |

As shown in Table 8, compared with the petrochemical EG raw material (Comparative Example 8), the performance index of polyester prepared from the green EG is obviously different from that of polyester prepared from the petrochemical EG, and the main reason is by-products of the ethylene glycol produced by hydrogenation of carbon dioxide to prepare methanol are higher than those of the petrochemical ethylene glycol. By using the specific esterification catalyst and the composite stabilizers, the performance index of polyester produced by the present disclosure is basically the same as that of polyester produced by petrochemical process.

The melt direct spinning process is used to spin 83.3 dtex/144f and 55.5 dtex/72f FDY fibers, and the green carbon reduction polyester fiber prepared from the green ethylene glycol meets the market requirements and is basically the same as the polyester fiber synthesized from the petrochemical ethylene glycol.

TABLE 9

| 83.3dtex/144 f FDY fiber physical and chemical index | | | | | | | | |
|---|---|---|---|---|---|---|---|---|
| No. | Specification | Fineness | Strength/ cN/dtex | Elongation/% | Oil content/% | Yarn evenness CV % | Boiling water shrinkage rate/% | Interlacing point |
| Example 3 | 83/144 | 82.8 | 3.90 | 35.70 | 1.01 | 0.94 | 6.6 | 10 |
| Example 4 | 83/144 | 82.7 | 3.91 | 35.27 | 1.06 | 0.95 | 6.6 | 10 |
| Example 5 | 83/144 | 83.2 | 3.93 | 35.54 | 1.02 | 0.93 | 6.4 | 10 |
| Example 6 | 83/144 | 82.8 | 3.89 | 35.41 | 0.98 | 0.92 | 6.7 | 9 |
| Example 7 | 83/144 | 83.7 | 3.87 | 35.52 | 1.00 | 0.95 | 6.5 | 10 |
| Example 8 | 83/144 | 83.4 | 3.95 | 35.90 | 1.02 | 0.93 | 6.8 | 11 |
| Comparative Example 5 | 83/144 | 82.9 | 3.92 | 35.83 | 1.01 | 0.93 | 6.4 | 10 |
| Comparative Example 6 | 83/144 | 83.2 | 3.88 | 36.10 | 1.05 | 0.96 | 6.5 | 10 |
| Comparative Example 7 | 83/144 | 82.8 | 3.86 | 36.25 | 1.03 | 0.92 | 6.5 | 10 |

TABLE 9-continued

| 83.3dtex/144 f FDY fiber physical and chemical index | | | | | | | | |
|---|---|---|---|---|---|---|---|---|
| No. | Specification | Fineness | Strength/ cN/dtex | Elongation/% | Oil content/% | Yarn evenness CV % | Boiling water shrinkage rate/% | Interlacing point |
| Comparative Example 8 | 83/144 | 83.3 | 3.91 | 36.21 | 1.02 | 0.95 | 6.6 | 10 |

Note:
Comparative Example 8 is the polyester fiber produced from the petrochemical EG and PTA Table 10 below is the quality index of the 55.5 dtex/72f FDY fiber.

TABLE 10

| 55.5dtex/72 f FDY fiber physical and chemical index | | | | | | | | |
|---|---|---|---|---|---|---|---|---|
| No. | Specification | Fineness | Strength/ cN/dtex | Elongation/ % | Oil content/% | Yarn evenness CV % | Boiling water shrinkage rate/% | Interlacing point |
| Example 3 | 55/72 | 55.4 | 3.97 | 33.57 | 1.06 | 1.27 | 7.2 | 14 |
| Example 4 | 55/72 | 54.8 | 4.00 | 33.07 | 1.05 | 1.24 | 7.4 | 14 |
| Example 5 | 55/72 | 55.3 | 3.95 | 32.88 | 1.04 | 1.24 | 7.3 | 13 |
| Example 6 | 55/72 | 55.0 | 3.99 | 33.15 | 1.06 | 1.26 | 7.3 | 14 |
| Example 7 | 55/72 | 54.9 | 3.96 | 32.62 | 1.07 | 1.31 | 7.1 | 14 |
| Example 8 | 55/72 | 55.5 | 4.00 | 32.96 | 1.05 | 1.27 | 7.2 | 14 |
| Comparative Example 5 | 55/72 | 55.4 | 3.98 | 32.81 | 1.02 | 1.26 | 7.5 | 14 |
| Comparative Example 6 | 55/72 | 55.6 | 4.03 | 32.74 | 1.05 | 1.26 | 7.3 | 13 |
| Comparative Example 7 | 55/72 | 54.9 | 3.88 | 33.70 | 1.04 | 1.24 | 7.5 | 14 |
| Comparative Example 8 | 55/72 | 55.5 | 4.02 | 32.55 | 1.06 | 1.27 | 7.3 | 14 |

Note:
Comparative Example 8 is the polyester fiber produced from the petrochemical EG and PTA The fiber is woven into a fabric, and after printing and dyeing, the fabric is subjected to tracking detection, and the detection results are as shown in Table 11.

TABLE 11

| Fabric tracking detection | | | | |
|---|---|---|---|---|
| No. | Tracer 1 Liquid phase (qualitative) | Tracer 1 Detection result (nuclear magnetic resonance absorption characteristic peak) | Tracer 2 Solid phase (quantitative) | Tracer 2 Detection result |
| Example 3 | 0 | None | 50 ppm | 42 ppm |
| Example 4 | 0 | None | 100 ppm | 87 ppm |
| Example 5 | 60 ppm | Yes | 50 ppm | 39 ppm |
| Example 6 | 80 ppm | Yes | 80 ppm | 68 ppm |
| Example 7 | 75 ppm | Yes | 100 ppm | 85 ppm |
| Example 8 | 75 ppm* | Yes | 100 ppm* | 85 ppm* |
| Comparative Example 5 | | None | | None |
| Comparative Example 6 | | None | | None |
| Comparative Example 7 | | None | | None |
| Comparative Example 8 | | None | | None |

Note:
Tracer 1: 2,2,4,4-tetramethylcyclobutanedicarboxylic acid, *pentaerythritol;
Tracer 2: nano barium sulfate, *sub-nanometer composite calcium carbonate-magnesium carbonate (calcium: 40 ppm, magnesium: 60 ppm, total: 100 ppm)

It can be seen that the tracer can be used for green carbon chemistry tracking. The above examples are only for illustrating the technical concept and characteristics of the present application, and the purpose is to enable those skilled in the art to understand the content of the present application and implement it, and cannot limit the protection scope of the present application. Any equivalent change or modification made according to the essence of the present application should be covered in the protection scope of the present application.

What is claimed is:

1. A method for preparing methanol by a hydrogenation reaction comprising carbon dioxide and hydrogen as raw materials to prepare the methanol, wherein:
 the hydrogenation reaction is carried out in a reaction system comprising two-stage fixed bed reactors in sequence, wherein:
  a first-stage fixed bed reactor comprises at least two reaction towers arranged in parallel, wherein each reaction tower of the first-stage fixed bed reactor is filled with a copper-zinc-calcium-magnesium-aluminum hydrogenation catalyst, wherein:
   the copper-zinc-calcium-magnesium-aluminum hydrogenation catalyst comprises:
    a supporting carrier, and
    an active component comprising copper oxide, zinc oxide, calcium oxide, magnesium oxide and aluminum oxide,
  wherein the copper-zinc-calcium-magnesium-aluminum hydrogenation catalyst is columnar and comprises a porous structure; and
  a second-stage fixed bed reactor comprises at least one reaction tower, wherein each reaction tower of the second-stage fixed bed reactor is filled with a copper-zirconium-titanium-vanadium deposition hydrogenation catalyst wherein:
   the copper-zirconium-titanium-vanadium deposition hydrogenation catalyst comprises:
    a supporting carrier comprising graphite, activated carbon and a binder,
    a nano silicon dioxide carrier, and
    a porous deposition catalyst layer on a surface of the nano silicon dioxide carrier, the porous deposition catalyst layer comprising copper oxide, zirconium oxide, titanium oxide and vanadium oxide,
   wherein the copper-zirconium-titanium-vanadium deposition hydrogenation catalyst is columnar and comprises a porous structure;
   wherein each of the first-stage fixed bed reactor and the second-stage fixed bed reactor comprise:
    an inner chamber comprising an inner circumference and an outer circumference and a plurality of horizontal arranged trays inside the inner circumference of the inner chamber, and
    an outer chamber comprising an outer circumference and an inner circumference, wherein the inner circumference of the outer chamber surrounds the outer circumference of the inner chamber, wherein:
     a top, a middle and a bottom of the outer chamber comprise a plurality of groups of homogenizing trays, and
     a filter screen is arranged at the bottom of the outer chamber between the outer circumference and the inner circumference of the bottom chamber;
 filling the copper-zinc-calcium-magnesium-aluminum hydrogenation catalyst between the inner chamber and the homogenizing trays of the outer chamber of the first-stage fixed bed reactor;
 filling the copper-zirconium-titanium-vanadium deposition hydrogenation catalyst between the inner chamber and the homogenizing trays of the outer chamber of the second-stage fixed bed reactor; and
 hydrogenating the carbon dioxide to form methanol, wherein:
  a pressure of the first-stage fixed bed reactor is from 5.0-15.0 MPa;
  a pressure of the second-stage fixed bed reactor is from 10.0-17.5 MPa; and
  a reaction selectivity of methanol after the hydrogenation reaction of the second-stage fixed bed reactor is completed is more than 97.0%.

2. The method for preparing methanol according to claim 1, wherein the first-stage fixed bed reactor comprises 2-6 reaction towers arranged in parallel; and/or, the second-stage fixed bed reactor comprises 1-2 reaction towers.

3. The method for preparing methanol according to claim 1, wherein effective volumes of the inner chamber and the outer chamber are the same and/or a residence time of the reaction gas in the inner chamber and the outer chamber is the same.

4. The method for preparing methanol according to claim 1, wherein a residence time of the raw materials in the first-stage fixed bed reactor is 275-350 s and/or a conversion rate of carbon dioxide after the hydrogenation reaction of the first-stage fixed bed reactor is completed is 64.0%-75.8% and/or a volume of each reaction tower of the first-stage fixed bed reactor is 135-150 $m^3$, and a volume of the copper-zinc-calcium-magnesium-aluminum hydrogenation catalyst filled therein is 75-90 $m^3$, and the volume of the copper-zinc-calcium-magnesium-aluminum hydrogenation catalyst filled therein is 75-90 $m^3$.

5. The method for preparing methanol according to claim 1, wherein a volume of each reaction tower of the second-stage fixed bed reactor is 135-150 $m^3$, and a volume of the copper-zirconium-titanium-vanadium deposition hydrogenation catalyst filled therein is 75-90 $m^3$ and/or a residence time of the reaction system in the second-stage fixed bed reactor is 75-100 s.

6. The method for preparing methanol according to claim 1, wherein in the second-stage fixed bed reactor, an effective self-circulation ratio of the reaction system is 3.5-6.0 and/or a cumulative conversion rate of carbon dioxide after the hydrogenation reaction of the second fixed bed reactor is completed is 92.4%-95.5%.

7. The method for preparing methanol according to claim 1, wherein a temperature of the first-stage fixed bed reactor is 150-350° C. and/or a temperature of the second-stage fixed bed reactor is 120-240° C.

8. The method for preparing methanol according to claim 1, wherein the carbon dioxide is derived from a byproduct of a petroleum refining process.

9. The method for preparing methanol according to claim 8, wherein the carbon dioxide is present in the byproduct of petroleum refining process at a volume content of 80%-90%.

10. The method for preparing methanol according to claim 1, wherein the carbon dioxide and hydrogen are mixed and pressurized, and then fed into the first-stage fixed bed reactor from the bottom to perform the hydrogenation reaction, a reacted gas stream flows out of the bottom of the first-stage fixed bed reactor, enters a condenser to be condensed, and then enters a methanol phase separation device after depressurization to perform phase separation.

11. The method for preparing methanol according to claim 10, wherein a molar ratio of the carbon dioxide to the hydrogen is 1:3-4.5.

12. The method for preparing methanol according to claim 10, wherein a gas stream at a top of the methanol phase separation device is mixed with additional hydrogen to obtain a mixture, and the mixture is pressurized and fed into a middle and lower part of the second-stage fixed bed reactor to perform the hydrogenation reaction, and a reacted liquid component flows out of a bottom of the second-stage fixed bed reactor and enters the methanol phase separation device to perform the phase separation.

13. The method for preparing methanol according to claim 12, wherein the additional hydrogen accounts for 4%-8% of a volume of the hydrogen fed into the first-stage fixed bed reactor.

14. The method for preparing methanol according to claim 12, wherein a tail gas at the top of the second-stage fixed bed reactor is subjected to depressurization treatment and then introduced into a pressure swing adsorption (PSA) device to perform hydrogen adsorption, desorption and recovery.

15. The method for preparing methanol according to claim 14, wherein a recovered hydrogen is used as a source of the additional hydrogen fed into the second-stage fixed bed reactor.

* * * * *